US008128917B2

(12) United States Patent
Cannell et al.

(10) Patent No.: US 8,128,917 B2
(45) Date of Patent: Mar. 6, 2012

(54) AQUEOUS POLYAMINE-CONTAINING CARRIER SYSTEMS FOR WATER-INSOLUBLE MATERIALS

(75) Inventors: David W. Cannell, Plainfield, NJ (US); Sawa Hashimoto, Westfield, NJ (US); Cynthia Chong Espino, Princeton, NJ (US); Katherine Natalie Barger, Cranford, NJ (US); Nghi Van Nguyen, Edison, NJ (US)

(73) Assignee: L'oréal (FR)

( * ) Notice: Subject to any disclaimer, the term of this patent is extended or adjusted under 35 U.S.C. 154(b) by 1062 days.

(21) Appl. No.: 11/154,249

(22) Filed: Jun. 16, 2005

(65) Prior Publication Data

US 2006/0286057 A1    Dec. 21, 2006

(51) Int. Cl.
*A61K 8/00* (2006.01)
*A61K 8/18* (2006.01)
*A61K 8/72* (2006.01)
*A61K 8/02* (2006.01)
*A61K 9/16* (2006.01)
*A61K 9/50* (2006.01)
*A61Q 5/00* (2006.01)
*A61Q 9/00* (2006.01)
*A61Q 7/00* (2006.01)
*A61Q 5/12* (2006.01)
*C11D 1/62* (2006.01)

(52) U.S. Cl. .............. 424/70.1; 424/70.11; 424/70.12; 424/70.27; 424/70.28; 424/490

(58) Field of Classification Search .............. 424/70, 424/70.1, 70.11, 70.12, 70.27, 70.28, 401, 424/490

See application file for complete search history.

(56) References Cited

U.S. PATENT DOCUMENTS

| 4,174,296 | A |   | 11/1979 | Kass |
|---|---|---|---|---|
| 4,275,055 | A |   | 6/1981 | Nachtigal et al. |
| 4,314,573 | A |   | 2/1982 | Spitzer et al. |
| 4,940,576 | A | * | 7/1990 | Walsh .................. 424/70.11 |
| 4,960,845 | A |   | 10/1990 | O'Lenick, Jr. |
| 5,019,394 | A |   | 5/1991 | Hamaguchi et al. |
| 5,070,171 | A |   | 12/1991 | O'Lenick, Jr. |
| 5,093,452 | A |   | 3/1992 | O'Lenick, Jr. |
| 5,135,669 | A |   | 8/1992 | Brois et al. |
| 5,149,765 | A |   | 9/1992 | O'Lenick, Jr. |
| 5,248,783 | A |   | 9/1993 | O'Lenick |
| 5,362,484 | A |   | 11/1994 | Wood et al. |
| 5,739,371 | A |   | 4/1998 | O'Lenick, Jr. |
| 5,980,919 | A |   | 11/1999 | Greenfield et al. |
| 6,015,574 | A |   | 1/2000 | Cannell et al. |
| 6,024,952 | A |   | 2/2000 | Story et al. |
| 6,221,389 | B1 |   | 4/2001 | Cannell et al. |
| 6,436,436 | B1 |   | 8/2002 | Nguyen et al. |
| 6,440,456 | B1 |   | 8/2002 | Nguyen et al. |
| 6,447,806 | B1 |   | 9/2002 | Gassmann et al. |
| 6,468,515 | B1 |   | 10/2002 | Uchiyama et al. |
| 6,524,614 | B2 |   | 2/2003 | Cannell et al. |
| 6,558,697 | B2 |   | 5/2003 | Cannell et al. |
| 6,602,494 | B1 |   | 8/2003 | Jahedshoar et al. |
| 2002/0064541 | A1 | * | 5/2002 | Lapidot et al. ............. 424/401 |
| 2004/0045099 | A1 | * | 3/2004 | Kuzuhara et al. ............. 8/405 |
| 2004/0052748 | A1 |   | 3/2004 | Vondruska |
| 2004/0076595 | A1 | * | 4/2004 | Khan .................. 424/70.11 |
| 2004/0170587 | A1 |   | 9/2004 | Vondruska |
| 2004/0223938 | A1 |   | 11/2004 | Li et al. |
| 2006/0216254 | A1 |   | 9/2006 | Majmudar et al. |
| 2006/0286055 | A1 |   | 12/2006 | Cannell et al. |
| 2006/0286056 | A1 |   | 12/2006 | Cannell et al. |
| 2006/0292100 | A1 |   | 12/2006 | Nguyen et al. |

FOREIGN PATENT DOCUMENTS

| EP | 1402881 A1 | 3/2004 |
|---|---|---|
| EP | 1 733 717 A1 | 12/2006 |

OTHER PUBLICATIONS

"New Cosmetic Formulations," Research Disclosure, Mason Publications, Hampshire, GB, No. 443, Mar. 2001, pp. 377-382, XP001126547.
McCutcheon's "Detergents and Emulsifiers," North American Edition (1986), published by Allured Publishing Corporation.
McCutcheon's "Functional Materials," North American Edition (1992).
CTFA Cosmetic Ingredient Handbook, First Edition, pp. 41-42.
CFTA 8th ed. vol. 2 (2000) pp. 1701-1703.
Hayley's condensed chemical Dictionary, 1993, p. 409.
U.S. Appl. No. 11/154,437, 2005.
U.S. Appl. No. 11/154,155, 2005.
U.S. Appl. No. 11/154,156, 2005.

* cited by examiner

*Primary Examiner* — Johann Richter
*Assistant Examiner* — Luke Karpinski
(74) *Attorney, Agent, or Firm* — Lerner, David, Littenburg, Krumhotz & Mentlik, LLP

(57) ABSTRACT

The present invention is drawn to a carrier composition containing: (a) at least one polyamine compound comprising at least two amino groups; (b) at least one nonionic surfactant; (c) at least one anionic silicone; and (d) at least one water-insoluble material, and wherein the composition, when combined with an aqueous phase, forms an aqueous delivery system which is both stable, and clear to slightly hazy/limpid in appearance.

38 Claims, No Drawings

AQUEOUS POLYAMINE-CONTAINING CARRIER SYSTEMS FOR WATER-INSOLUBLE MATERIALS

BACKGROUND OF THE INVENTION

The present invention relates to a novel carrier system based on a combination of at least one polyamine compound having at least two amino groups, at least one nonionic surfactant, and at least one anionic silicone, wherein the carrier system allows water-insoluble materials to be incorporated into aqueous solutions.

Certain water-insoluble ingredients which are oftentimes desirable for the treatment of keratinous substrates are inherently difficult to incorporate into aqueous systems such as shampoos and conditioners without forming a traditional emulsion in either cream or lotion form. Moreover, many of these water-insoluble ingredients suppress lathering which makes the use of aqueous systems such as shampoos and body washes less desirable to consumers. Even in those aqueous systems which do employ these types of water-insoluble ingredients, their presence is minimal due to various performance drawbacks such as poor spreadability, foaming, removal and rinsing or, in the case of styling products, difficulties in removal via shampooing.

Also, when formulating clear to slightly limpid aqueous delivery systems for use in treating keratinous substrates, water-insoluble compounds do not lend themselves to being used therein, due to their inability to significantly associate with the water present in the system.

Thus, there remains a need for an aqueous delivery system which can carry water-insoluble materials while remaining both stable and clear, to slightly limpid, in appearance.

SUMMARY OF THE INVENTION

In order to achieve these and other advantages, the present invention is drawn to a carrier composition containing:
  (a) at least one polyamine compound having at least two amino groups;
  (b) at least one nonionic surfactant;
  (c) at least one anionic silicone; and
  (d) at least one water-insoluble material,
wherein the composition, when combined with an aqueous phase, forms an aqueous delivery system which is both stable, and clear to slightly hazy/limpid in appearance.

In another embodiment, the present invention is also drawn to a process for making an aqueous delivery system which is both stable, and clear to slightly limpid in appearance, involving the steps of:
  (a) providing a carrier composition containing: (i) at least one polyamine compound, (ii) at least one nonionic surfactant and, (iii) at least one anionic silicone;
  (b) providing at least one water-insoluble ingredient;
  (c) optionally, heating the composition of step (a) to form a heated mixture;
  (d) adding (b) to either step (a), step (c) or both step (a) and (c);
  (e) adding an aqueous solution to either step (c) or step (d) form a diluted mixture; and
  (f) cooling the diluted mixture to form the aqueous delivery system.

Finally, in yet another embodiment, the present invention is drawn to a process for treating a keratinous substrate by contacting the substrate with an aqueous delivery system containing the above-disclosed carrier composition.

DETAILED DESCRIPTION

Other than in the operating examples, or where otherwise indicated, all numbers expressing quantities of ingredients and/or reaction conditions are to be understood as being modified in all instances by the term "about".

The term "water-insoluble" means those compounds which are either completely or partially insoluble in water.

The term "carried" means that the aqueous delivery system containing the water-insoluble ingredients is both stable and clear, to slightly limpid, in appearance.

"Amino groups" as defined herein includes primary amino groups, secondary amino groups, and tertiary amino groups, and further includes amino groups which are terminal, pendant, and intercalated in a skeleton of the at least one polyamine compound, but does not, for example, include quaternary amino groups, amido groups, imino groups, nitrilo groups, or heteroatom analogs of any of the foregoing.

"At least one" as used herein means one or more and thus includes individual components as well as mixtures/combinations.

"Conditioning" as used herein means imparting to at least one keratinous fiber at least one property chosen from combability, manageability, moisture-retentivity, luster, shine, and softness. The state of conditioning is evaluated by measuring, and comparing, the ease of combability of the treated hair and of the untreated hair in terms of combing work (gm-in).

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Ethylene oxide group" as defined herein refers to a group of formula —CH$_2$CH$_2$—O—.

"Propylene oxide group" as defined herein includes groups of formula —CH$_2$CH$_2$CH$_2$—O—, groups of formula (CH$_3$)CHCH$_2$—O—, and groups of formula —CH$_2$ (CH$_3$)CH—O—.

"Keratinous substrate" as defined herein may be human keratinous fiber, and may be chosen from, for example, hair, eyelashes, and eyebrows, as well as the stratum corneum of the skin and nails.

"Polymers," as defined herein, include homopolymers and copolymers formed from at least two different types of monomers.

Advantageously, the present invention allows water-insoluble materials or ingredients to be carried in an aqueous solution. No alcohol is required to render the system stable and clear, to slightly limpid, in appearance.

The carrier composition of the invention is easy to formulate and gentle on the hair, skin, or eyelashes because the surfactants used therein are generally mild.

The compositions and delivery systems of the present invention readily deliver water-insoluble ingredients to the targeted keratinous substrate. Accordingly, these compositions and delivery systems can be used in hair shampoos, conditioners, deep treatments, hair dyeing compositions, including oxidative dyes and bleaches, permanent waving compositions, curl relaxing compositions, hair setting compositions, bath and body products, sunscreens, cosmetics, skin moisturizers, and the like.

These systems can also be used to deliver active water-insoluble pharmaceutical ingredients, particularly in topical applications. Such systems could further help protect against oxidation and rancidity by protecting sensitive ingredients in pharmaceuticals or foods.

Without being bound to a particular theory, the inventors believe that the aqueous delivery system is in the form of a microemulsion whereby the anionic silicone forms an ion pair or pseudo-soap with the polyamine compound having at least two amino groups which is then coupled to the aqueous solution as a mixed micelle (or other organized structure) by the nonionic surfactant. This structure is believed to be of sufficient stability and size to provide hydrophilic regions which carry the water-insoluble ingredients. These microemulsions range from pourable liquids to firm ringing gels.

The at least one polyamine compound of the present invention comprises at least two amino groups. In one embodiment, the at least one polyamine compound of the present invention comprises at least three amino groups. In one embodiment, the at least one polyamine compound of the present invention comprises at least four amino groups, such as greater than four amino groups. In one embodiment, the at least one polyamine compound of the present invention comprises at least five amino groups, such as greater than five amino groups. In one embodiment, the at least one polyamine compound of the present invention comprises at least six amino groups, such as greater than six amino groups. In one embodiment, the at least one polyamine compound of the present invention comprises at least ten amino groups, such as greater than ten amino groups.

In one embodiment of the present invention, the at least one polyamine compound may, for example, be chosen from aminated polysaccharides comprising at least two amino groups, such as, for example, hydrolysates of aminated polysaccharides comprising greater than two amino groups. In one embodiment, the at least one polyamine compound may, for example, be chosen from polymers. Suitable polymers for use as the at least one amine compound are polymers comprising at least two amino groups as defined herein. Non-limiting examples of suitable polymers include homopolymers comprising at least two amino groups, copolymers comprising at least two amino groups, and terpolymers comprising at least two amino groups. Thus, the at least one polyamine compound comprising at least two amino groups may be chosen from, for example, polymers comprising at least two amino groups formed from (i) at least one monomer unit comprising at least one amino group as defined herein, and, optionally, (ii) at least one additional monomer unit different from the at least one monomer (i); and polymers comprising at least two amino groups formed from (i) at least one monomer comprising at least two amino groups as defined herein, and, optionally, (ii) at least one additional monomer unit different from the at least one monomer (i). According to the present invention, the at least one additional monomer different from the at least one monomer (i) may or may not comprise at least one amino group as defined herein.

In one embodiment of the present invention, the at least one polyamine compound is chosen from polyamines. As used herein, "polyamines" comprise at least two repeating units, wherein each unit comprises at least one amino group as defined herein. In one embodiment, polyamines are chosen from polyethyleneimines. Polyethyleneimines suitable for use in the compositions of the present invention may optionally be substituted. Non-limiting examples of polyethyleneimines which may be used in the composition according to the present invention are the Lupasol™ products commercially available from BASF. Suitable examples of Lupasol™ polyethyleneimines include Lupasol™ PS, Lupasol PL, Lupasol™ PR8515, Lupasol™ G20, Lupasol™ G35 as well as Lupasol™ SC.® Polythyleneimine Reaction Products (such as Lupasol™ SC-61B®, Lupasol™ SC-62J®, and Lupasol™ SC-86X®). Other non-limiting examples of polyethyleneimines which may be used in the composition according to the present invention are the Epomin™ products commercially available from Aceto. Suitable examples of Epomin™ polyethyleneimines include Epomin™ SP-006, Epomin™ SP-012, Epomin™ SP-018, and Epomin™ P-1000.

Polyamines suitable for use in the present invention may also be chosen from polyvinylamines. Examples thereof include Lupamines® 9095, 9030, 9010, 5095, 1595 from BASF.

The polyamine compounds can also be substituted. An example of such a compound is PEG-15 Cocopolyamine from Cognis.

In another embodiment, the at least one polyamine compound comprising at least two amino groups is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, 8$^{th}$ edition, vol. 2, (2000). In one embodiment, the at least one polyamine compound comprising at least two amino groups is chosen from wheat protein, soy protein, oat protein, collagen, and keratin protein.

In one embodiment, the at least one polyamine compound comprising at least two amino groups is not chosen from proteins and protein derivatives. In one embodiment, the at least one polyamine compound comprising at least two amino groups is not chosen from compounds comprising lysine, compounds comprising arginine, and compounds comprising histidine. In one embodiment, the at least one polyamine compound comprising at least two amino groups is chosen from compounds comprising lysine, compounds comprising arginine, compounds comprising histidine, and compounds comprising hydroxylysine.

In the present invention, the at least one polyamine compound is preferably used in an amount of from greater than 0% to 30% by weight, preferably from greater than 0% to 10% by weight, and more preferably from greater than 0% to 5% by weight, based on the weight of the composition as a whole. Preferably, the carrier composition of the present invention, when combined with water, forms a clear solution, though the purpose of the invention is achieved just as effectively with a slightly cloudy/limpid solution.

In general, nonionic surfactants having a Hydrophilic-Lipophilic Balance (HLB) of from 8 to 20, are contemplated for use by the present invention. Nonlimiting examples of non-ionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the C12-C50 range, preferably in the C16-C40 range, more preferably in the C24 to C40 range, and having from about 1 to about 110 alkoxy groups. The alkoxy groups are selected from the group consisting of C2-C6 oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from ICI Specialty Chemicals, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. C8-30 alcohols, with sugar or starch polymers. These compounds can be represented by the formula $(S)_n$—O—R wherein S is a sugar moiety such as glucose, fructose, mannose, galactose, and the like; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8-20 alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from ICI Specialty Chemicals, Wilmington, Del.), sorbitan monoisostearate (e.g., CRILL® 6 from Croda, Inc., Parsippany, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of C2-C6 oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of C12 to C18 fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. Preferably the nonionic surfactants contain ethoxylate in a molar content of from 10-25, more preferably from 10-20 moles.

The nonionic surfactant will typically be present in the composition in an amount of from greater than 0% to 70% by weight, preferably from greater than 0% to 40% by weight, and more preferably from greater than 0% to 20% by weight, based on the weight of the composition as a whole.

In general, non-limiting examples of anionic silicones which may be used in the present invention include silicone carboxylates, silicone phosphates, silicone sulfates, silicone sulfosuccinates, and silicone sulfonates.

Suitable silicone carboxylates may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the at least one silicone compound comprising at least one carboxylic acid group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the at least one silicone compound comprising at least one carboxylic acid group is chosen from silicone compounds of formula (I) and salts thereof:

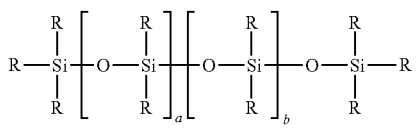
(I)

wherein: a is an integer ranging from 1 to 100; b is an integer ranging from 0 to 500; R, which may be identical or different, are each chosen from optionally substituted hydrocarbon groups comprising from 1 to 9 carbon atoms, optionally substituted phenyl groups, and groups of formula (II):

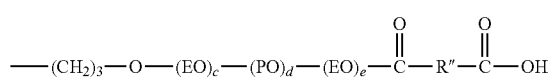
(II)

wherein: c, d, and e, which may be identical or different, are each integers ranging from 0 to 20; EO is an ethylene oxide group; PO is a propylene oxide group; and R″ is chosen from optionally substituted divalent hydrocarbons, such as alkylene groups and alkenylene groups comprising from 2 to 22 carbon atoms, and optionally substituted divalent aromatic groups, such as groups of formula (III):

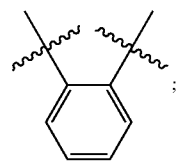
(III)

and groups of formula (IV):

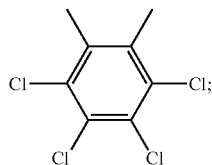
(IV)

with the proviso that at least one of the R groups is chosen from groups of formula (II) and with the further proviso that when only one of the R groups is chosen from groups of formula (II), the other R groups are not all methyl groups.

Non-limiting examples of the at least one silicone compound include those commercially available from Noveon under the name Ultrasil® CA-1 Silicone and Ultrasil® CA-2 Silicone, both of which correspond to formula (V) below. This silicone carboxylate is sold in the free acid form as an emulsifier and dispersing aid for complexing fatty cationic amines and quaternary amines. Thus, in one embodiment, the at least one silicone compound is chosen from silicone compounds of formula (V) and salts thereof:

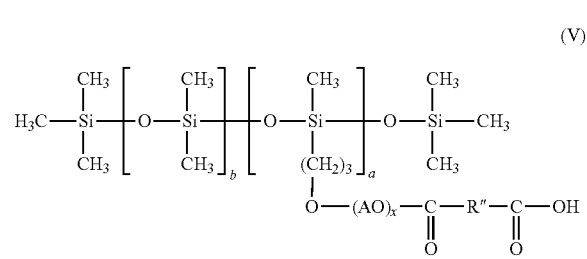
(V)

wherein: a is an integer ranging from 1 to 100; b is an integer ranging from 0 to 500; AO is chosen from groups of formula (VI):

-(EO)$_c$—(PO)$_d$-(EO)$_e$- (VI)

wherein: c, d, and e, which may be identical or different, are each integers ranging from 0 to 20; EO is an ethylene oxide group; and PO is a propylene oxide group; x is an integer ranging from 0 to 60; R″ is chosen from optionally substituted divalent hydrocarbons, such as alkylene groups and alkenylene groups comprising from 2 to 22 carbon atoms, and optionally substituted divalent aromatic groups, such as groups of formula (III):

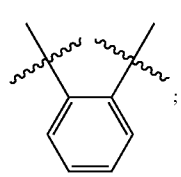
(III)

and groups of formula (IV):

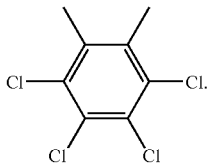
(IV)

Non-limiting examples of the at least one silicone compound include those described in U.S. Pat. Nos. 5,248,783 and 5,739,371, the disclosures of which are incorporated herein by reference, and which are silicone compounds of formula (I).

Suitable silicone phosphates may be chosen from water-soluble silicone compounds comprising at least one phosphate group, oil soluble silicone compounds comprising at least one phosphate group, water-dispersible silicone compounds comprising at least one phosphate group, and silicone compounds comprising at least one phosphate group which are soluble in organic solvents.

In one embodiment, the at least one silicone compound comprising at least one phosphate group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups ("EO"=—$CH_2$—$CH_2$—O—) and propylene oxide groups ("PO"=$C_3H_6O$).

The at least one phosphate group may be chosen from terminal phosphate groups and pendant phosphate groups. Further, the at least one phosphate group may be chosen from groups of formula —O—P(O)(OH)$_2$, groups of formula —O—P(O)(OH)(OR), and groups of formula —O—P(O)(OR)$_2$, wherein R may be chosen from H, inorganic cations, and organic cations. Non-limiting examples of inorganic cations include alkali metals, such as, for example, potassium lithium, and sodium. A non-limiting example of organic cations is at least one additional silicone compound which may be identical to or different from the at least one silicone compound bonded to the other oxygen of the phosphate group.

In one embodiment, the at least one silicone compound comprising at least one phosphate group is chosen from silicone compounds of formula (I):

P(OR$^1$)$_3$
(I)

wherein R$^1$, which may be identical or different, are each chosen from H, organic cations, inorganic cations, optionally substituted hydrocarbons (such as alkyl groups and alkenyl groups comprising from 1 to 22 carbon atoms), optionally substituted aromatic groups; groups of formula (II) and salts thereof:

$CH_3(CH_2)_x$—O-(EO)$_c$—(PO)$_d$-(EO)$_e$-$CH_2CH_2$— (II)

wherein: c, and d, which may be identical or different, are each integers ranging from 0 to 20; e is an integer ranging from 0 to 19; and x is an integer ranging from 0 to 21; groups of formula (III) and salts thereof:

HO-(EO)$_c$—(PO)$_d$-(EO)$_e$-(CH$_2$)$_x$— (III)

wherein: c, d, and e, which may be identical or different, are each integers ranging from 0 to 20; and x is an integer ranging from 0 to 21; and groups of formula (IV) and salts thereof:

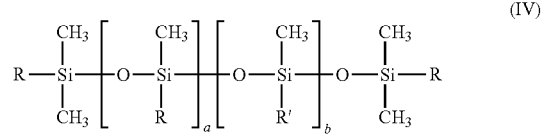
(IV)

wherein: a is an integer ranging from 0 to 200; b is an integer ranging from 0 to 200; R', which may be identical or different, are each chosen from optionally substituted hydrocarbons, such as alkyl groups and alkenyl groups comprising from 1 to 22 carbon atoms, optionally substituted aromatic groups, groups of formula (III) as defined above and salts thereof; and R, which may be identical or different, are each chosen from optionally substituted hydrocarbons, such as alkyl groups and alkenyl groups comprising from 1 to 22 carbon atoms, optionally substituted aromatic groups, optionally substituted divalent hydrocarbons, such as alkylene groups and alkenylene groups comprising from 1 to 22 carbon atoms, optionally substituted divalent aromatic groups, groups of formula (III) as defined above and salts thereof, and groups of formula (V):

-(EO)$_c$—(PO)$_d$-(EO)$_e$-(CH$_2$)$_3$— (V)

wherein:
the (CH$_2$)$_3$ end is bonded to the silicon of the compound of formula (IV) and the (EO) or (PO) end, if present, is bonded to the oxygen of the compound of formula (I); c, d, and e, which may be identical or different, are each integers ranging from 0 to 20; EO is an ethylene oxide group; and PO is a propylene oxide group; and with the proviso that at least one R is chosen from groups of formula (V) and salts thereof; and with the further proviso that at least one R$^1$ is chosen from groups of formula (IV) and salts thereof and at least one other R$^1$ is chosen from H, organic cations, and inorganic cations.

Non-limiting examples of the inorganic cations include alkali metals, such as potassium, lithium, and sodium. Non-limiting examples of the at least one silicone compound include those commercially available from Phoenix Chemical, Inc. of New Jersey under the name of Pecosil®, such as Pecosil® PS-100, Pecosil® PS-112, Pecosil® PS-150, Pecosil® PS-200, Pecosil® WDS-100, Pecosil® WDS-200, Pecosil® PS-100 B, and Pecosil® PS-100 K and those commercially available from Siltech under the name Silphos A-100 and Silphos A-150. Other non-limiting examples of the at least one silicone compound include those described in U.S. Pat. Nos. 5,070,171, 5,093,452, and 5,149,765 the disclosures of which are incorporated herein by reference.

Suitable silicone sulfates for use in the present invention include those represented by formula VI:

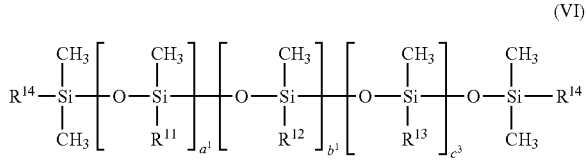
(VI)

wherein R$^{11}$ is selected from lower alkyl having one to eight carbon atoms or phenyl, R$^{12}$ is —(CH$_2$)$_3$—O-(EO)$_x$—(PO)$_y$-(EO)$_z$—SO$_3^{31}$-M$^+$ wherein M is a cation and is selected from Na, K, Li, or NH$_4$; x, y and z are integers independently ranging from 0 to 100; $R^{13}$ is —$(CH_2)_3$—O-$(EO)_x$—$(PO)_y$-$(EO)_z$—H; $R^{14}$ is methyl or hydroxyl; $a^1$ and $c^1$ are independently integers ranging from 0 to 50; $b^1$ is an integer ranging from 1 to 50. An example thereof is Ultrasil SA-1 silicone commercially available from Noveon.

Suitable silicone sulfosuccinates which may be employed include, but are not limited to, those corresponding to formula VII:

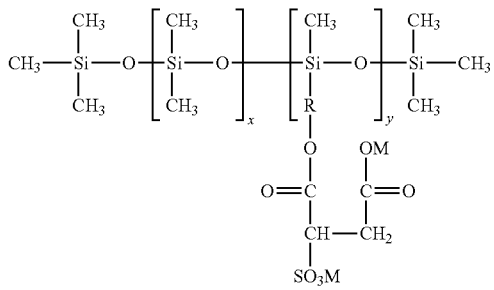

(VII)

wherein R represents a divalent radical selected from

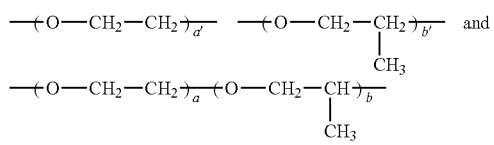

wherein a' and b' range from 0 to 30; x and y are such that the molecular weight ranges from 700 to 1600, and M is an alkali metal such as sodium or potassium, or an ammonium group.

A particularly preferred anionic silicone is Dimethicone PEG-8 phosphate, commercially available from Noveon under the tradename Ultrasil PE-100.

The anionic silicone is present in the composition in an amount ranging from greater than 0 to 50% by weight, preferably from greater than 0 to 30% by weight, and more preferably from greater than 0 to 15% by weight, based on the weight of the composition as a whole.

It has surprisingly been found that the carrier composition of the present invention facilitates the formulation of an aqueous delivery system capable of carrying up to 50% by weight, preferably up to 30% by weight, more preferably up to 20% by weight, and most preferably up to 10% by weight, all weights being based on the weight of the composition, of water-insoluble ingredients. The resultant aqueous delivery system is both stable, and clear to slightly hazy/limpid in appearance.

Thus, in another aspect, the present invention relates to an aqueous delivery system comprising the carrier composition, at least one water-insoluble ingredient and an aqueous phase. The carrier composition is present in an amount sufficient to allow the at least one water-insoluble material to be incorporated into the aqueous system. The amount sufficient for incorporation may vary depending on the type of composition; for example, shampoo and mascara formulations require a lower concentration of the carrier composition than do conditioner, deep treatment, bleach, permanent wave, dye, and relaxant compositions.

Water-insoluble materials or ingredients include, but are not limited to, the following:

(1) Lipophilic "ingredients" or "materials" such as silicones, oil-soluble vitamins such as Vitamin E and Vitamin A, sunscreens, ceramides and natural oils: The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, 2-oleamido-1,3-octadecanediol, octylmethoxy cinnamate, octyl salicylate, and silicones such as dimethicone, cyclomethicone, phenyl trimethicone, dimethiconol, dimethicone copolyol, aminosilicone and laurylmethicone copolyol. The lipophilic ingredients will, for example, moisturize or condition the skin, hair, and/or eyelashes and leave behind no oily feel.

(2) Water-insoluble polymers, resins, and latexes, wherein the polymers and resins include but are not limited to those containing carboxyl moieties, such as acrylates and other carboxy polymers.

Preferred water-insoluble ingredients for use in the present invention include silicones ranging from low molecular weight fluids to high molecular weight gums; hydrocarbons such as mineral oil, petrolatum, paraffins, iso-paraffins, aromatic hydrocarbons, and the like; plant oils such as olive, avocado, coconut, and the like; fatty acids; fatty esters; fatty alcohols; and fatty waxes.

The aqueous phase of the inventive delivery system can contain additional ingredients such as anionic surfactants, organic salts, inorganic salts, proteins, hair dyes, water-soluble polymers, quaternary ammonium compounds, complex and simple carbohydrates, amino acids, preservatives and fragrances.

Another embodiment of the present invention is drawn to a process for making an aqueous delivery system. This process involves: (a) providing a carrier composition containing at least one polyamine compound, at least one nonionic surfactant, and at least one anionic silicone; (b) providing at least one water-insoluble ingredient; (c) optionally, heating the carrier composition to form a heated composition; (d) adding the water-insoluble ingredient to either the carrier composition, the heated composition or both; (e) providing an aqueous solution; (f) adding the aqueous solution to the heated mixture to form a diluted mixture and (g) cooling the diluted mixture to form the desired aqueous delivery system. Preferably the aqueous delivery system obtained can carry a high load (i.e., 50% is considered a high load) of the water-insoluble ingredient.

In another embodiment, the present invention is drawn to a process for treating keratinous substances such as, but not limited to, hair, skin, or eyelashes by contacting the keratinous substance with the above-disclosed aqueous delivery system. The term treating in the context of this invention includes, but is not limited to, shampooing, conditioning, dyeing, bleaching, permanent waving, relaxing, setting, moisturizing, and making-up, for example, applying mascara or foundation.

As mentioned previously, the carrier composition and aqueous delivery system of the present invention can be used as an ingredient itself in, for example, shampoos, conditioners (rinse-off and leave-in), deep treatments for hair, body washes, bath gels, hair dyeing compositions, permanent wave formulations, relaxers, make-up preparations, particularly mascara and foundation, and skin creams or lotions.

The aqueous delivery systems of the invention can be further associated, in the hair products described above, with proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the keratinous substrate. Cationic proteins or proteins in general may be stabilizers for the aqueous delivery system and enhance its delivery by changing the charge of the aqueous delivery system. The skin and the hair attract cationic ingredients, and proteins are generally substantive to these tissues.

Other ingredients in the aqueous delivery system may include cationic polymers, such as polyquaternium 4, polyquaternium 6, polyquaternium 7, polyquaternium 10, polyquaternium 11, polyquaternium 16, polyquaternium 22, and polyquaternium 32, cationic conditioners, such as quaternium 27, behenamidopropyl PG-dimonium chloride, hydroxyethyl tallowdimonium chloride, hexadimethrine chloride, stearalkonium chloride, and cetrimonium chloride, isoparaffins, sodium chloride, propylene glycol, preservatives such as phenoxyethanol, methylparaben, ethylparaben, and propylparaben, pH adjusters such as phosphoric acid, humectants such as trehalose, and emollients such as octyldodecanol. Many other examples of materials from the classes listed above would be readily known to one of ordinary skill in the art.

Further, shampoos, conditioners, and deep treatments within the scope of the present invention may be used on hair which has been treated, e.g., with color (dye or bleach) or chemicals (permanent wave or straightening), or which is dry or fine and show significant substantivity for the hair.

The invention will be further clarified by the following examples, which are intended to be illustrative of the invention, but not limiting thereof.

EXAMPLES

General procedure: The general procedure for formulating the carrier system is as follows: Add Lupasol G-35 (INCI: PEI) and Ultrasil PE-100 (silicone phosphate) into a beaker and begin mixing at moderate speed. Next, add the active ingredient. Mix well. Then add Laureth-4. Mix well. Lastly, add deionized water. Mix until formula becomes clear. Note: This may require mixing for over 4 hours.

1. The Carrier System

Following the general procedure, a series of solutions were made as depicted in Table 1. The results show that a complete carrier system is needed to form a clear, stable solution that contains a water insoluble silicone.

TABLE 1

Experiments showing a clear, stable carrier system

| Combinations of ingredients | Appearance |
| --- | --- |
| Water 40 g + Lupasol G-35 10 g + DC 200 (300,000 cst) 10 g | Hazy |
| Water 40 g + Laureth-4 10 g + DC 200 (300,000 cst) 10 g | Hazy |
| Water 40 g + Silicone Phosphate 30 g + DC 200 (300,000 cst) 10 g | Hazy |
| Water 40 g + Lupasol G-35 10 g + Laureth-4 10 g + DC 200 (300,000 cst) 10 g | Hazy |
| Water 40 g + Lupasol G-35 10 g + Silicone Phosphate 30 g + DC 200 (300,000 cst) 10 g | Hazy |
| Water 40 g + Laureth-4 10 g + Silicone Phosphate 30 g + DC 200 (300,000 cst) 10 g | Hazy |
| Water 40 g + Lupasol G-35 10 g + Laureth-4 10 g + Silicone Phosphate 30 g + DC 200 (300,000 cst) 10 g | Clear |

2. Carrier System with Different Silicones

The carrier system is able to carry different types of silicones, such as DC 200 (INCI: dimethicone) and DC 556 (INCI: phenyltrimethicone). When formulated using the general procedure as described above, clear, stable systems are obtained, as shown in table 2.

TABLE 2

Carrier system with different types of silicones

| | | | | |
| --- | --- | --- | --- | --- |
| D.I. Water | 40% | 40% | 40% | 40% |
| Lupasol G-35 | 10% | 10% | 10% | 10% |
| Laureth-4 | 10% | 10% | 10% | 10% |
| Silicone Phosphate | 30% | 30% | 30% | 30% |
| Silicones | 10% (DC 200 (1000 cst)) | 10% (DC 200 (60,000 cst)) | 10% (DC 200 (300,000 cst)) | 10% (DC 556) |

3. Carrier System with Tea Tree Oil

The carrier system is able to carry different types of oils, such as tea tree oil. When formulated using the general procedure as described above, clear, stable systems are obtained, as shown in table 3.

TABLE 3

Carrier system with Tea tree oil

| | |
| --- | --- |
| D.I. Water | 40% |
| Lupasol G-35 | 10% |
| Laureth-4 | 10% |
| Silicone Phosphate | 30% |
| Tea Tree oil | 10% |

4. Carrier System with Esters/Waxes/Hydrocarbons

The carrier system is able to carry different types of hydrocarbons, such as C11-13 Isoparaffin. When formulated using the general procedure as described above, clear, stable systems are obtained, as shown in table 4.

TABLE 4

Carrier system with C11-13 Isoparaffin

| | |
| --- | --- |
| D.I. Water | 40% |
| Lupasol G-35 | 10% |
| Laureth-4 | 10% |
| Silicone Phosphate | 30% |
| C11-13 Isoparaffin | 10% |

5. Carrier System with Other Polyamines

Carrier system is also clear and stable when Lupasol G-35 is replaced with another polyamine, such as Lupamin 9095, Lupasol PR 8515, Lupasol P, and Lupasol SK. See table 5.

TABLE 5

Carrier system with different polyamines

| | A | B | C | D |
| --- | --- | --- | --- | --- |
| D.I. Water | 40% | 40% | 40% | 40% |
| Polyamines | 10% (Lupamin 9095) | 10% (Lupasol PR 8515) | 10% (Lupasol P) | 10% (Lupasol SK) |
| Laureth-4 | 10% | 10% | 10% | 10% |
| Silicone Phosphate | 30% | 30% | 30% | 30% |
| C11-13 Isoparaffin | 10% | 10% | 10% | 10% |

Furthermore, the above formula B is dilutable in water.

6. Conditioning Effects of the Carrier System

The conditioning effect of the carrier system, as a carrier of Dimethicone, was assessed by the wet combability method using the Instron 4444 Tensile Tester. Evaluation was carried out on virgin hair, cleansed with 15% SLES, and treated a single time with the carrier formulation. Specifically, swatches were treated once with 2 g product, which remained on the hair for 1 minute. Swatches were then shampooed with 2.5 g of 15% SLES for 15 seconds and rinsed for 10 seconds. The total combing energy required to comb the hair was measured after cleansing with SLES ($W_i$), as well as after treatment and one shampoo ($W_f$). The percent change in combing energy was calculated using the following formula:

$$\%\Delta\text{Combing Energy} = (W_f - W_i)/(W_i) \times 100\%$$

where $W_i$=combing energy required prior to treatment
and $W_f$=combing energy required after treatment and one shampoo.

Treatments, which improve wet combability, will result in negative percent change values.

A clear, stable carrier solution composed of the following formula was used to treat the hair:

| Classification | Trade Name | % wt/wt |
| --- | --- | --- |
| Water | Water | 40 |
| Silicone Phosphate | Ultrasil PE-100 | 30 |
| Nonionic Surfactant | Brij 30 | 10 |
| PEI | Lupasol G 35 | 10 |
| Dimethicone | Dow Corning 200 Fluid (60,000 cst) | 10 |

Following treatment with the carrier formulation and a single shampoo, the percent change in combing energy was −34.19%, indicating that the treated hair is significantly more conditioned. Thus, treatment with the carrier system made the hair more manageable and easier to comb by 34.19%.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. A composition comprising:
   (a) at least one polyamine compound comprising at least two amino groups;
   (b) at least one nonionic surfactant;
   (c) at least one anionic silicone;
   (d) at least one water-insoluble material which is present in an amount of from about 4% to about 50% by weight, based on the total amount of the composition; and
   (e) water.

2. The composition of claim 1 wherein (a) is polyethyleneimine.

3. The composition of claim 1 wherein (a) is polyvinylamine.

4. The composition of claim 1 wherein (a) is present in an amount of from greater than 0 to about 30% by weight, based on the weight of the composition.

5. The composition of claim 1 wherein (a) is present in an amount of from greater than 0 to about 5% by weight, based on the weight of the composition.

6. The composition of claim 1 wherein (b) has an HLB of about 8 or greater.

7. The composition of claim 1 wherein (b) is present in an amount of from greater than 0 to about 70% by weight, based on the weight of the composition.

8. The composition of claim 1 wherein (b) is present in an amount of from greater than 0 to about 20% by weight, based on the weight of the composition.

9. The composition of claim 1 wherein (c) is a silicone phosphate.

10. The composition of claim 1 wherein (c) is a silicone carboxylate.

11. The composition of claim 1 wherein (c) is a silicone sulfate.

12. The composition of claim 1 wherein (c) is present in an amount of from greater than 0 to about 50% by weight, based on the weight of the composition.

13. The composition of claim 1 wherein (c) is present in an amount of from greater than 0 to about 15% by weight, based on the weight of the composition.

14. The composition of claim 1 wherein (d) is present in an amount of about 50% or less by weight, based on the weight of the composition.

15. The composition of claim 1 wherein (d) is present in an amount of about 10% or less by weight, based on the weight of the composition.

16. A process for making an aqueous delivery system which is both stable, and clear to slightly limpid in appearance, involving the steps of:
   (a) providing a carrier composition containing:
      (i) at least one polyamine compound comprising at least two amino groups, (ii) at least one nonionic surfactant and, (iii) at least one anionic silicone;
   (b) providing at least one water-insoluble ingredient;
   (c) optionally, heating the composition of step (a) to form a heated mixture;
   (d) adding (b) in an amount of from about 4% to about 50% by weight of the aqueous delivery system to either step (a), step (c) or both step (a) and (c);
   (e) adding an aqueous solution to either (c) or (d) to form a diluted mixture; and
   (f) cooling the diluted mixture to form the aqueous delivery system.

17. A process for treating a keratinous substrate comprising contacting the keratinous substrate with a composition containing:
   (a) at least one polyamine compound comprising at least two amino groups;
   (b) at least one nonionic surfactant;
   (c) at least one anionic silicone; and
   (d) at least one water-insoluble material which is present in an amount of from about 4% to about 50% by weight, based on the total amount of the composition.

18. The process of claim 16 wherein (a) is polyethyleneimine.

19. The process of claim 16 wherein (a) is polyvinylamine.

20. The process of claim 16 wherein (a) is present in an amount of from greater than 0 to about 30% by weight, based on the weight of the composition.

21. The process of claim 16 wherein (a) is present in an amount of from greater than 0 to about 5% by weight, based on the weight of the composition.

22. The process of claim 16 wherein (b) has an HLB of about 8 or greater.

23. The process of claim 16 wherein (b) is present in an amount of from greater than 0 to about 70% by weight, based on the weight of the composition.

24. The process of claim 16 wherein (b) is present in an amount of from greater than 0 to about 20% by weight, based on the weight of the composition.

25. The process of claim 16 wherein (c) is a silicone phosphate.

26. The process of claim 16 wherein (c) is a silicone carboxylate.

27. The process of claim 16 wherein (c) is a silicone sulfate.

28. The process of claim 16 wherein (c) is present in an amount of from greater than 0 to about 50% by weight, based on the weight of the composition.

29. The process of claim 16 wherein (c) is present in an amount of from greater than 0 to about 15% by weight, based on the weight of the composition.

30. The process of claim 16 wherein (d) is present in an amount of about 10% or less by weight, based on the weight of the composition.

31. The process of claim 16 wherein the keratinous substrate is hair.

32. A personal care composition comprising the composition of claim 1.

33. The composition of claim 32 wherein the composition is chosen from a shampoo, a conditioner, or a combination shampoo and conditioner.

34. The composition of claim 33, wherein the conditioner is a leave-in conditioner or a rinse-off conditioner.

35. The composition of claim 1, wherein the water-insoluble material is selected from the group consisting of silicones, hydrocarbons, plant oils, fatty acids, fatty esters, fatty alcohols, fatty waxes, and mixtures thereof.

36. The composition of claim 35, wherein the water-insoluble material is a silicone.

37. The composition of claim 1, wherein the water-insoluble material is selected from the group consisting of dimethicone, cyclomethicone, phenyl trimethicone, dimethiconol, dimethicone copolyol, aminosilicone, laurylmethicone copolyol, capric/caprylic triglyceride, avocado oil, olive oil, macadamia nut oil, jojoba oil, apricot kernel oil, rice bran oil, tea tree oil, mineral oil, and mixtures thereof.

38. The composition of claim 1, wherein water is present in an amount of about 40% by weight, based on the weight of the composition.

* * * * *

UNITED STATES PATENT AND TRADEMARK OFFICE
CERTIFICATE OF CORRECTION

PATENT NO. : 8,128,917 B2
APPLICATION NO. : 11/154249
DATED : March 6, 2012
INVENTOR(S) : David W. Cannell et al.

Page 1 of 1

It is certified that error appears in the above-identified patent and that said Letters Patent is hereby corrected as shown below:

On the Title page, Item (74), "Littenburg, Krumhotz" should read -- Littenberg, Krumholz --.

Signed and Sealed this
Twenty-third Day of July, 2013

Teresa Stanek Rea
*Acting Director of the United States Patent and Trademark Office*